United States Patent
Kida et al.

(10) Patent No.: US 8,123,759 B2
(45) Date of Patent: Feb. 28, 2012

(54) INTRODUCER SHEATH STABILIZER

(75) Inventors: Toshiaki Kida, Oonojou (JP);
Christopher J. Elliott, Hopkinton, MA (US); Marcia Busier, Watertown, MA (US); Ashley Seehusen, Somerville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1001 days.

(21) Appl. No.: 12/061,407

(22) Filed: Apr. 2, 2008

(65) Prior Publication Data
US 2008/0183183 A1    Jul. 31, 2008

Related U.S. Application Data

(62) Division of application No. 10/833,982, filed on Apr. 28, 2004, now Pat. No. 7,367,980.

(51) Int. Cl.
*A61F 11/00* (2006.01)
(52) U.S. Cl. ...................................... 606/108
(58) Field of Classification Search .................. 606/108, 606/113, 114, 127, 159, 200; 623/1.11, 1.12; 29/407.08, 234, 252, 508; 604/164.01, 164.03, 604/264; 600/585
See application file for complete search history.

(56) References Cited

U.S. PATENT DOCUMENTS

| | | | |
|---|---|---|---|
| 5,476,472 A | 12/1995 | Dormandy, Jr. et al. | |
| 5,746,734 A | 5/1998 | Dormandy, Jr. et al. | |
| 5,944,735 A | 8/1999 | Green et al. | |
| 6,090,072 A * | 7/2000 | Kratoska et al. | 604/164.01 |
| 6,183,443 B1 * | 2/2001 | Kratoska et al. | 604/164.03 |
| 7,214,201 B2 * | 5/2007 | Burmeister et al. | 600/585 |
| 2002/0198586 A1 | 12/2002 | Inoue | |

FOREIGN PATENT DOCUMENTS

| | | |
|---|---|---|
| EP | 1 254 634 A1 | 11/2002 |
| WO | 01/13800 A1 | 3/2001 |
| WO | 2004/026146 A1 | 4/2004 |

* cited by examiner

*Primary Examiner* — Kevin T Truong
(74) *Attorney, Agent, or Firm* — Seager, Tufte & Wickhem, LLC

(57) ABSTRACT

A device for introducing an embolic coil into a catheter comprises an elongated body defining a longitudinal passage extending therethrough from a first opening at a proximal end thereof to a second opening at a distal end thereof, the elongated body being including a mating portion for conforming to a size and shape of an opening in a hub of a catheter to mate therewith and an embolic coil introducer sheath including a coil receiving lumen extending therethrough, a distal tip of the introducer sheath being dimensioned to be received within a proximal end of the longitudinal passage. Similarly, a method of implanting an embolic coil, comprises inserting a stabilizer into a catheter hub so that a flexible mating portion substantially conforms to a shape of an inner surface of the hub wherein the stabilizer includes a passage extending therethrough from a proximal opening to a distal opening thereof. An introducer sheath including an embolic coil received in a lumen thereof is inserted into the proximal opening of the passage and through the passage to exit the distal opening thereof so that a distal opening of the lumen is positioned substantially adjacent to a proximal opening of a catheter and an embolic coil is advanced out of the distal opening of the lumen into the catheter and deployed in the body through the catheter.

9 Claims, 2 Drawing Sheets

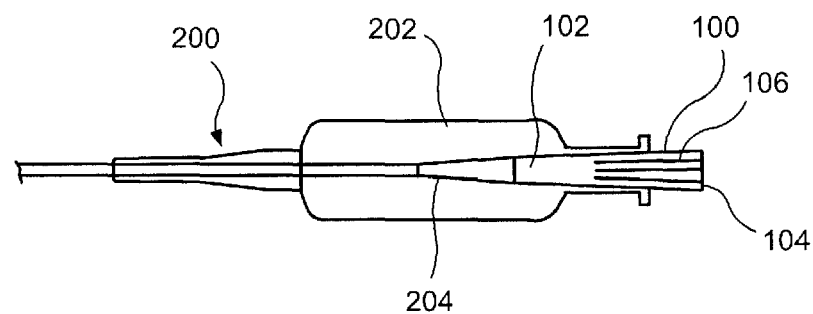
FIG. 1
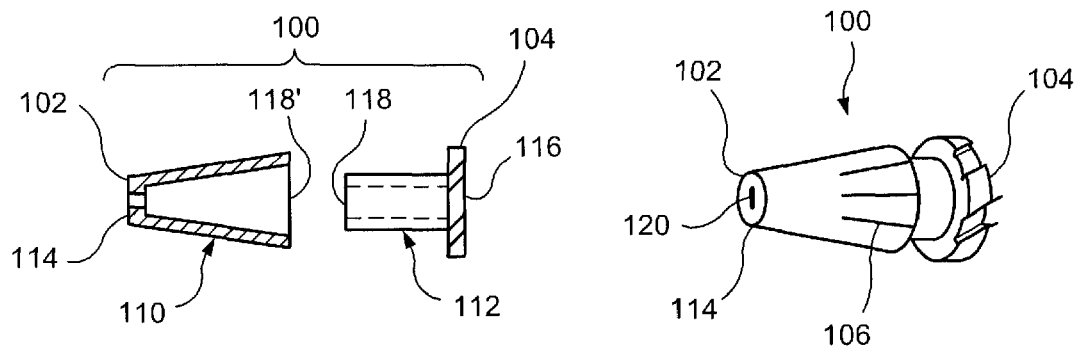
FIG. 2
FIG. 3
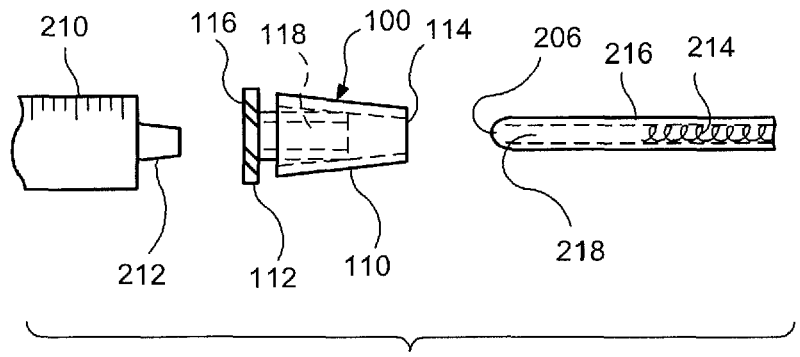
FIG. 4

INTRODUCER SHEATH STABILIZER

The present application is a Divisional application of U.S. patent application Ser. No. 10/833,982 filed on Apr. 28, 2004 now U.S. Pat. No. 7,367,980 entitled "Introducer Sheath Stabilizer". The entire disclosure of this application is expressly incorporated herein by reference.

BACKGROUND OF THE INVENTION

Embolic coils have been used to stop undesired blood flow, as in, for example, the treatment of aneurysms, arteriovenous malformations, traumatic fistulae and in tumor embolization. These conditions require that the blood flow through a portion of a blood vessel be stopped, for example by introducing an artificial device into the vessel to slow the flow, and by letting the natural clotting process form a more complete blockage of the blood vessel with a clot.

Embolic coils can be used to form a blockage in a vein or artery to treat conditions like those listed above. These devices have become increasingly common in procedures to block the flow of blood by promoting formation of a clot in a desired location. Embolic coils are made from a bio-compatible material, such as platinum, to minimize the problems associated with tissue irritation and rejection. These coils are often shaped as complex three dimensional curves that fill in portions of the blood vessels and slow blood flow therein. Often, polymeric fibers are added to the metallic coils to enhance the coil's thrombogenicity, which is the coil's ability to promote formation of clots.

Embolic coils are typically introduced into a blood vessel by using a microcatheter which extends from a proximal point outside the patient's body to a distal point near the embolization site. An introducer sheath containing the coil is used to carry and protect the coil prior to insertion into the patient, and also to transfer the coil to the microcatheter. From the introducer sheath the coil is pushed into the microcatheter and navigated to the embolization site, where it is deployed from the microcatheter. It is often beneficial to pre-hydrate the coil before insertion into the microcatheter to lubricate the coil, so that it travels more easily to the embolization site. In addition, the fluid used to lubricate the coil may be medicated to increase the thrombogenic properties of the coil, reduce infections, or to address other needs.

SUMMARY OF THE INVENTION

In one aspect, the present invention is directed to a device for introducing an embolic coil into a catheter comprising an elongated body defining a longitudinal passage extending therethrough from a first opening at a proximal end thereof to a second opening at a distal end thereof, the elongated body being including a mating portion for conforming to a size and shape of an opening in a hub of a catheter to mate therewith in combination with an embolic coil introducer sheath including a coil receiving lumen extending therethrough, a distal tip of the introducer sheath being dimensioned to be received within a proximal end of the longitudinal passage.

The present invention is further directed to a method of implanting an embolic coil, comprising inserting a stabilizer into a catheter hub so that a flexible mating portion substantially conforms to a shape of an inner surface of the hub, the stabilizer including a passage extending therethrough from a proximal opening to a distal opening thereof and inserting an introducer sheath including an embolic coil received in a lumen thereof into the proximal opening of the passage and through the passage to exit the distal opening thereof so that a distal opening of the lumen is positioned substantially adjacent to a proximal opening of a catheter. The embolic coil is advanced out of the distal opening of the introducer sheath lumen into the catheter and deployed in the body via the catheter.

BRIEF DESCRIPTION OF THE DRAWINGS

FIG. 1 is a schematic side elevation view showing an introducer sheath stabilizer, according to the present invention, disposed in a microcatheter hub;

FIG. 2 is an exploded side elevation view of an introducer sheath stabilizer, according to the present invention;

FIG. 3 is a perspective view of the introducer sheath stabilizer of FIG. 2;

FIG. 4 is a schematic side elevation view of an introducer sheath stabilizer used in a coil pre-hydration function;

DETAILED DESCRIPTION

Figure 5:
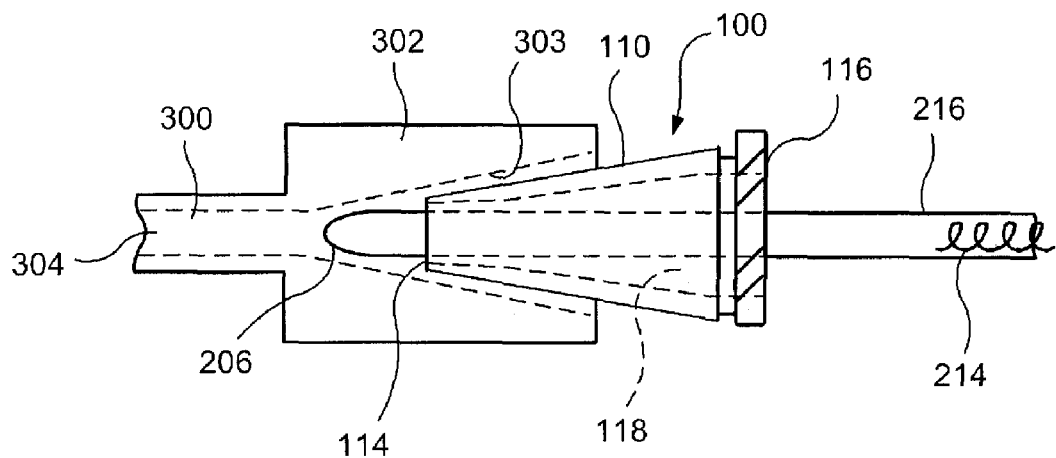
FIG. 5 is a schematic side elevation view of an introducer sheath stabilizer used in a coil introduction function.

The present invention may be further understood with reference to the following description and the appended drawings, wherein like elements are referred to with the same reference numerals. The present invention is related to medical devices used to introduce an embolic coil into the vascular system of a patient. More specifically, the invention is related to devices used to introduce an embolic coil using a catheter, and to hydrate the embolic coil prior to deployment.

Embolic coils have been widely used to treat medical conditions requiring the disruption of the blood flow to specific regions of the body. For example, the treatment of aneurysm, arterial or venous malformations, traumatic fistulae and tumor embolization requires that the supply of blood to the affected areas be interrupted. Aneurysms occur when a portion of an artery's wall becomes weakened and expands in a balloon-like manner. As more blood flows in, the aneurysm continues to expand and the wall of that portion becomes stretched and thins. If the wall at the aneurysm expands too much, it may burst and cause a hemorrhage. This is a very dangerous condition which may lead to death, coma, paralysis, or other serious medical condition when it occurs in the brain or another vital organ.

Traditionally, this condition has been very difficult to diagnose, since patients are generally asymptomatic until the aneurysm bursts. At that point, most of the damage has already taken place, and the available medical therapies are limited. Even where the aneurysm is identified prior to bursting, medical options have been limited because aneurysms are often in locations that are difficult to reach by surgery and repairing the damaged blood vessel may be impossible. Recent advances in visualization methods, however, have made the early identification of aneurysms and similar problems more common. Once an aneurysm has been located, it may be possible to block the supply of blood thereto via an embolic coil, even if surgery to repair the blood vessel is not practical.

Embolic coils may also be used successfully in the treatment of various types of cancer. As tumors often require a large supply of blood to grow, it may be possible to impede further growth by restricting or eliminating this blood supply. Embolic coils may be deployed to shut down blood vessels alimenting the tumor to kill or limit the growth of the malignancy. Deployment of the coil may be aided by various visualization methods, to ensure correct positioning and to evaluate the efficacy of the treatment. The treatment of traumatic bleeding may also benefit from the use of embolic coils. As would be understood by those skilled in the art, damage to blood vessels causing significant blood loss may result in death or a critical condition. This may be especially serious when the injury is internal and the bleeding cannot be controlled without resorting to complex surgical procedures. Embolic coils may be employed to reduce or stop the hemorrhage by blocking the veins or arteries leading to the damaged area(s).

The deployment of embolic coils into a patient's vascular system is typically carried out using a catheter. The distal end of the catheter is inserted into a blood vessel and is navigated to the site where the coil is to be deployed with any of various methods of visualization being employed to confirm that a distal end of the catheter is positioned at the proper location. The catheter may be a microcatheter, having a catheter hub at the proximal end which remains outside of the body during the procedure. The embolic coil may be held in an introducer sheath for manipulation prior to insertion, and to insert the coil into the microcatheter after the coil has been prepared.

Introducer sheaths can be difficult to insert into the catheter hub at the microcatheter's proximal end. The microcatheter hub is a device adapted to receive attachments to the proximal end of the catheter. If the introducer sheath tip is not fully pressed into the catheter hub during coil delivery, or if there is a space between the sheath tip and the lumen of the microcatheter, the coil may be deployed in the hub causing premature detachment or jamming. For example, interlocking detachable coils feature a coil connected to a drive mechanism, from which it detaches when it is ejected from the catheter. If the introducer sheath is not seated fully in the catheter hub, the arms of the drive mechanism can detach prematurely and cause jamming in the hub. It is thus important to ensure that the coil is passed directly into the catheter lumen from the introducer sheath.

As described above, prior to insertion in the catheter, it is often necessary to pre-hydrate the coil. This preparatory step consists of irrigating the coil with a saline solution which may contain one or more medical compounds. For example, the coil may be irrigated with a heparin solution to prevent premature coil thrombosis prior to desired final deployment of the coil. Other fluids may also be used to hydrate the embolic coil. For example, compounds adapted to lubricate the coil as it travels through the microcatheter may be used, as well as disinfecting compounds, if needed.

Conventionally, pre-hydration of the embolic coil is carried out before insertion in the catheter, while the coil is still held in the introducer sheath which can be difficult. However, if the embolic coil is removed from the introducer sheath for pre-hydration, the coil may kink or be deformed when replaced in the introducer sheath. In particular, coils that comprise fibers extending from the coil loops may benefit from being pre-hydrated without removal from the introducer sheath. The fibers are designed to further reduce the flow of blood around the coil, and have a predetermined orientation. Deploying and then re-sheathing these fibered coils for pre-hydration may reverse the direction and change the orientation of the fiber bundles, reducing their effectiveness.

According to embodiments of the present invention, an introducer sheath stabilizer may be used for both facilitating pre-hydration of an embolic coil and to simplify transfer of the coil from the introducer sheath to a microcatheter. During both steps, the embolic coil is protected from damage. The procedure may be carried out by a single physician, without the need for involvement of assistants. FIG. 1 shows an exemplary embodiment of an introducer sheath stabilizer according to the invention. In the drawing, a sheath stabilizer 100 is shown in an operative position within a hub 202 of a microcatheter 200. A distal end 102 of the stabilizer 100 is inserted into the hub 202 of the microcatheter 200, such that it abuts the proximal end of a catheter lumen 204.

During use, an introducer sheath 216 containing an embolic coil 214 is inserted into the proximal end 104 of the stabilizer 100, and is pushed through the stabilizer 100 until it exits out of the distal end 102 of the stabilizer 100, as clearly shown in FIGS. 4 and 5. The introducer sheath 216 is then further pushed until it contacts the proximal end of the lumen 204. In this manner the stabilizer 100 helps to maintain the introducer sheath 216 in place preventing premature coil detachment and jamming of the coil 214 in the catheter hub 202. In the exemplary embodiment, the stabilizer 100 comprises slits 106 formed longitudinally on the walls thereof. The slits 106 facilitate the insertion of the introducer sheath 216 into the stabilizer 100, prior to attachment to the catheter hub 202, and also provide a better connection with the catheter hub 202. In this example, the stabilizer 100 mechanically and frictionally cooperates with the hub 202 to properly position the introducer sheath 216.

As will be described below in more detail, the sheath introducer the stabilizer 100 may also be used to facilitate pre-irrigation of the embolic coil 214 prior to deployment. In this function, the stabilizer 100 is used to couple a syringe or other source of irrigating fluid to the introducer sheath 216 containing the embolic coil 214. The stabilizer 100 thus serves a dual function, facilitating the pre-irrigation of the coil and the insertion of the coil 214 into the microcatheter 200. The physician performing the embolization procedure thus can carry out two tasks using only one device which can be provided, for example, together with the introducer sheath 216 as part of the packaging for the embolic coil 214.

FIGS. 2 and 3 show an exemplary embodiment of the stabilizer 100 according to the invention. In this embodiment, the stabilizer 100 comprises two portions joined to one another. A rigid female luer adapter 112 forms the proximal end 104 of the stabilizer 100 and is designed to provide a means of connecting the stabilizer 100 to another device provided with a luer. A flexible conical section 110 defines the distal portion 102 and completes the stabilizer 100. The flexible conical section 110 is designed to provide a snug fit with the proximal end of the microcatheter, such as by acting as an adapter fitting into the catheter hub 202. However, the stabilizer 100 may also be used to facilitate pre-hydration of the embolic coil 214 while still in the introducer sheath 216. In that function, the distal end 102 of the flexible conical section 110 becomes a receptacle for the distal tip of the introducer sheath 216. A syringe may then be connected to the luer adapter 112 to provide the irrigation.

As would be understood by those skilled in the art, the rigid female luer adapter 112 may be formed of any suitable material compatible with conventional luers (for example, polycarbonate, ABS plastic, Tecoplast). As would be understood, the material selected should be sufficiently resilient to maintain the dimensions of the luer adapter 112 during use of the stabilizer 100. A lumen 118 extends longitudinally through the luer adapter 112, and joins a lumen 118' which extends through the flexible conical section 110 to form a continuous passage through the stabilizer 100. The lumens 118, 118' have dimensions adapted to receive the introducer sheath 216 therethrough. The flexible conical section 110 may be formed from polyurethane, santoprene, silicone, natural latex, other thermoplastic elastomers or any material having a suitable flexibility.

In one embodiment, slits or openings 106 may be formed on shell-like walls of the conical section 110, to provide additional flexibility. The flexibility of the conical section 110 enables the stabilizer 100 to fit securely in a variety of catheter hubs having different dimensions, to provide a secure and stable interface between the catheter hub and the introducer sheath 216. In particular, the slitted portion of the flexible conical section 110 allows it to expand and/or contract to fit catheter hubs of different diameters. According to exemplary embodiments of the invention, the flexible conical section 110 forms a catheter hub adapter having outer surfaces which substantially match an inner passage of the hub, and which form a frictional and mechanical connection to the hub. As can be seen in the figures, a radius of the conical section 110 is a minimum at the distal end 102 and a maximum at the proximal end 104, so that conical section 110 can be inserted into the hub until the connection is made.

The exemplary flexible conical section 110 comprises a distal opening 114 with a sealing device, which may be a valve 120. The valve 120 may be of a single slit design, as shown, or may be a dual slit or multi slit design. The valve 120 is designed to accept the coil introducer sheath 216 for pre-hydration of the embolic coil 214 contained therein. In this mode, the tip of the introducer sheath 216 is inserted from the outside into the conical section 110 through the valve 120 which forms a seal around the introducer sheath 216. Conversely, when the stabilizer 100 is used to facilitate the introduction of the embolic coil 214 into the catheter 200, the distal tip 206 of the introducer sheath 216 is inserted through a proximal opening 116 of the stabilizer 100 and pushed out of the stabilizer 100 through the valve 120. The valve 120 thus permits passage of the introducer sheath 216 in both directions, while providing a sealing action around exterior surfaces of the introducer sheath 216.

The coil pre-hydration function of the stabilizer 100 is described in greater detail with reference to FIG. 4. As shown, an embolic coil 214 is contained within a tubular passage 218 extending through the sheath 216 from a proximal coil receiving opening to a distal coil deploying opening formed in a distal end 206 thereof. In this configuration, the embolic coil 214 is ready for deployment. However, if it is desired to pre-hydrate the coil 214, this may be done without removing the coil 214 from the passage 218. According to the invention, the distal tip 206 of the introducer sheath 216 is inserted into the stabilizer 100 via the opening 114 of the distal end 102 so that the distal tip 206 is received within the stabilizer 100 with the distal opening facing the proximal opening 116 in the luer adapter 112. The valve 120 provides a seal around the outer surface of the introducer sheath 216, such that a fluid may flow within the lumen 118 to the passage 218 without leaking from the stabilizer 100. A syringe 210 or other similar source of hydrating fluid is connected to the luer adapter 112 using a conventional luer attachment, such that the nozzle 212 enters the proximal opening 116 of the stabilizer 100. Fluid such as, for example, a heparinized solution, is then injected into the lumen 118 of the stabilizer 100 from the syringe 210 into the passage 218 of the introducer sheath 216, to reach the coil 214.

After pre-hydration, the stabilizer 100 may be used to assist in introducing the coil 214 into a microcatheter 200 via the coil deploying opening in the distal end 206. To use the stabilizer 100 in this way, the syringe 210 is disconnected from the stabilizer 100 and the sheath 216 is removed from the stabilizer 100 and reinserted into the stabilizer 100 via the opening 116 at the proximal end thereof. The sheath 216 is extended through the valve 120 so that the distal tip 206 protrudes from the distal end of the stabilizer 100.

The coil introduction function of introducer sheath stabilizer 100 is described in more detail with reference to FIG. 5. In this configuration, the smaller diameter distal end of the cone-shaped stabilizer 100 is inserted into the catheter hub 302 of a catheter 300. The flexible conical section 110 is formed of a pliable material to mate with a tapered inner surface 303 of the catheter hub 302 to form a stable, temporary frictional and mechanical connection with the catheter 300. The introducer sheath 216 is then inserted into the stabilizer 100 through the proximal opening 116 and is pushed through the passage 118 until its distal end 206 emerges from the distal opening 114 through the valve 120. The introducer sheath 216 is further pushed longitudinally until the coil deploying opening of the distal tip 206 seats in the tapered inner surface 303 substantially adjacent to a proximal opening of the catheter lumen 304. Thus, the coil 214 may be transferred directly from the passage 218 to the lumen 304 without unwanted movement of the tip 206 relative to seating surfaces of the catheter hub 302. This reduces the chances of premature detachment, damage or entrapment of the coil 214 in the microcatheter hub 302.

The exemplary multi functional introducer sheath stabilizer according to embodiments of the present invention allows for embolic coil pre-hydration without removal from the sheath as well as greater ease of coil insertion in a delivery catheter, by using a single device. The exemplary device may be used for multiple types of coils, including pushable coils and fibered coils for which pre-deployment and re-sheathing risk reversing or altering the fiber's orientation. The inclusion of a luer adapter allows for in line attachment of a rotating hemostatic valve (RHV) for continuous or intermittent heparinized saline flush of the microcatheter lumen.

Figure 6:
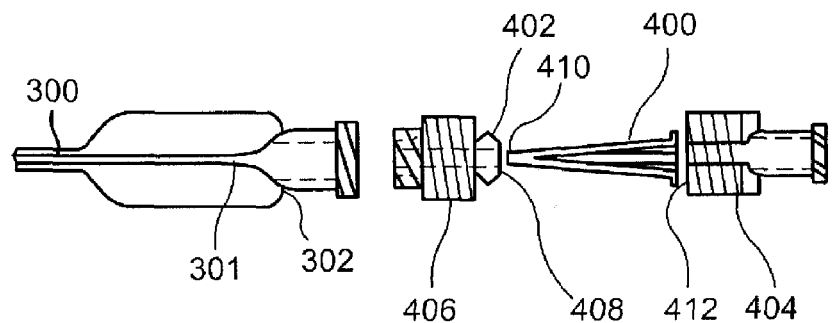
FIG. 6 is an exploded view showing another embodiment of an introducer sheath stabilizer, according to the present invention, incorporated into an assembly having aspects of a rotating hemostasis valve (RHV)
Figure 7:
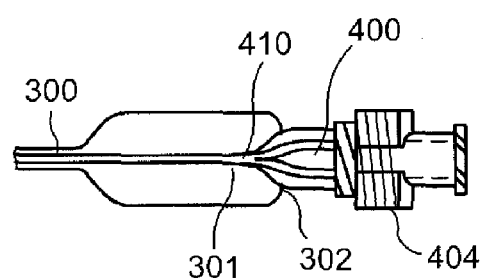
FIG. 7 is an assembled view of the introducer sheath stabilizer of FIG. 6.

In a different exemplary embodiment, the introducer sheath stabilizer may be incorporated into an RHV. FIGS. 6 and 7 show a stabilizer 400 adapted to fit in an RHV placed on the proximal end of a microcatheter 300. In this configuration, a distal male luer 406 is adapted to lock to the proximal end of a catheter hub 302 of the microcatheter 300. The distal male luer 402 doubles as a valve housing and serves as the bottom valve housing for a valve 402. The valve 402 may be a conventional valve used in conjunction with catheters. The stabilizer 400 fits through a passage 408 which extends through the valve 402 and through the male valve housing 406 and further extends beyond the RHV to protrude into the microcatheter hub 302. The distal end 410 of the stabilizer 400 protrudes sufficiently to engage the tapered portion 301 of the hub 302 and thus seal against any reflux of blood or other fluids from the microcatheter 300. A threaded closure may be used to join the male valve housing 406 to a female luer adapter 404, which allows mating to an external device for flushing the microcatheter 300 prior to introducing the coil 214 thereinto.

The assembly of the male valve housing 406 and the female luer adapter 404 forms a structure which contains the valve 402 and defines a passage 408 containing the stabilizer 400. The assembly may be designed so that the valve 402 can be closed by the user, for example by tightening the threads of the assembly. Placing the stabilizer 400 within the RHV provides several advantages. Seating the stabilizer 400 in the microcatheter hub 302 helps prevent the occurrence of retrograde blood flow up the sheath 216 reducing the possibility of thrombus build up in the interface between the two parts and reducing friction in the sheath 216. As in the embodiments described above, the stabilizer 400 maintains the introducer sheath 216 (not shown in FIG. 6) centered within the microcatheter hub 302, resulting in a smoother introduction of the embolic coil 214 into the microcatheter 300. The valve 402 prevents kickback of the sheath 216 and together with the stabilizer 400 reduces coil jamming and premature detachment.

As described above, the distal portion of the sheath 216 may be formed of a compressible material adapted to conform to the inner surfaces of a variety of microcatheter hubs. This universal compatibility of the stabilizer 400 with different catheters and hubs may be enhanced by slots 412 formed in the conical portion of the stabilizer 400. The slots 412 help the proximal portion of the stabilizer 400 to widen or narrow to fit different size passages, so that the stabilizer 400 provides a properly sized passage to an introducer sheath 216 containing a coil 214 regardless of the size of the catheter or hub.

The present invention has been described with reference to specific embodiments, and more specifically to a stabilizer used to facilitate introduction of an embolic coil into a microcatheter hub. However, other embodiments may be devised that are applicable to other procedures and devices, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A system for introduction of a coil into a catheter for deployment into a body lumen, comprising:
   a stabilizer including a rigid luer adapter at a proximal end thereof and a flexible catheter hub mating portion extending from the luer adapter to a distal end of the stabilizer wherein a passage extends through the stabilizer from the proximal end to an opening formed in the distal end; and
   an introducer sheath including a coil receiving lumen extending therethrough to a coil deploying opening, a distal portion of the sheath being sized for insertion through the passage to project distally from the distal opening, the distal portion of the sheath and the mating portion being sized so that, when the mating portion is inserted to an operative position within a hub of a catheter with the distal portion of the sheath projecting therefrom, the coil deploying opening abuts a proximal opening of the catheter.

2. The system according to claim 1, further comprises:
   a valve to seal the passage around the sheath.

3. The system according to claim 2, wherein the valve comprises a membrane with at least one slit formed therein.

4. The system according to claim 1, wherein an outer surface of the mating portion is shaped substantially similarly to an inner surface of the catheter hub.

5. The system according to claim 4, wherein the outer surface of the mating portion is substantially conical.

6. The system according to claim 1, wherein the mating portion includes a plurality of slits imparting increased flexibility thereto.

7. The stabilizer according to claim 1, wherein a minimum radius section of the mating portion is adjacent to the distal end of the stabilizer and a maximum radius thereof is adjacent to the luer adapter.

8. The stabilizer according to claim 1, wherein, when inserted into a hub of a catheter, the mating portion frictionally and mechanically engages the hub to retain a desired relative position of the sheath and the catheter during introduction of an coil thereto.

9. The stabilizer according to claim 1, wherein the rigid luer adapter and the mating portion are frictionally joined.

* * * * *